(12) United States Patent
Singh et al.

(10) Patent No.: US 7,868,016 B2
(45) Date of Patent: Jan. 11, 2011

(54) PHARMACEUTICAL FORMULATIONS OF ENDO-N-(9-METHYL-9-AZABICYCLO[3,3.1]NON-3-YL)-1-METHYL-1H-INDAZOLE-3-CARBOXAMIDE HYDROCHLORIDE

(75) Inventors: Kiran Pal Singh, Mullica Hill, NJ (US); Pui-Ho Yuen, Princeton Junction, NJ (US)

(73) Assignees: Baxter International Inc., Deerfield, IL (US); Baxter Healthcare S.A., Glattpark (Opfikon) (CH)

( * ) Notice: Subject to any disclaimer, the term of this patent is extended or adjusted under 35 U.S.C. 154(b) by 658 days.

(21) Appl. No.: 11/326,957

(22) Filed: Jan. 5, 2006

(65) Prior Publication Data

US 2007/0015808 A1 Jan. 18, 2007

(51) Int. Cl.
*A61K 31/439* (2006.01)
(52) U.S. Cl. ...................................................... 514/299
(58) Field of Classification Search ................ None
See application file for complete search history.

(56) References Cited

U.S. PATENT DOCUMENTS

| | | | |
|---|---|---|---|
| 4,886,808 A | 12/1989 | King | 514/299 |
| 5,935,972 A * | 8/1999 | Naylor et al. | 514/320 |
| 6,239,147 B1 * | 5/2001 | Obach et al. | 514/320 |
| 6,294,548 B1 | 9/2001 | James | 514/299 |
| 2004/0022755 A1 * | 2/2004 | Kamath | 424/70.16 |
| 2005/0142073 A1 * | 6/2005 | Watts et al. | 424/46 |
| 2005/0186637 A1 * | 8/2005 | Yu et al. | 435/7.1 |

FOREIGN PATENT DOCUMENTS

| | | |
|---|---|---|
| WO | WO 03/003957 | 1/2003 |
| WO | WO 2005/056008 | 6/2005 |

OTHER PUBLICATIONS

Physicians' Desk Reference, 56$^{th}$ edition (2002), p. 2986.*
Rowe, R.C. et al., "Handbook of pharmaceutical excipients," 4th edition 2003, Pharmaceutical Press, XP002403743; pp. 390-394; p. 391, paragraph Stability and Storage Conditions pp. 526-528.

* cited by examiner

*Primary Examiner*—Phyllis G. Spivack
(74) *Attorney, Agent, or Firm*—K&L Gates LLP

(57) ABSTRACT

A pharmaceutical formulation suitable for multi-dose administration comprising endo-N-(9-methyl-9-azabicyclo[3.3.1]non-3-yl)-1-methyl-1H-indazole-3-carboxanide hydrochloride, a preservative selected from the group consisting of alkyl paraben and phenol, and a buffer selected from the group consisting of acetate and phosphate buffers is disclosed.

6 Claims, No Drawings

PHARMACEUTICAL FORMULATIONS OF ENDO-N-(9-METHYL-9-AZABICYCLO[3,3,1]NON-3-YL)-1-METHYL-1H-INDAZOLE-3-CARBOXAMIDE HYDROCHLORIDE

This invention relates to improved formulations of endo-N-9-methyl-9-azabicyclo[3.3.1]non-3-yl)-1-methyl-1H-indazole-3-carboxamide hydrochloride. The formulations of this invention are useful as anti-emetics, particularly in the treatment of cytotoxic agent-induced emesis.

BACKGROUND OF THE INVENTION

Endo-N-(9-methyl-9-azabicyclo[3.3.1]non-3-yl)-1-methyl-1H-indazole-3-carboxamide hydrochloride, its use as an anti-emetic, particularly in the treatment of cytotoxic agent induced emesis, and methods for its synthesis are disclosed in U.S. Pat. No. 4,886,808. Endo-N-(9-methyl-9-azabicyclo[3.3.1]non-3-yl)-1-methyl-1H-indazole-3-carboxamide hydrochloride is commercially available and is also known by the generic name granisetron hydrochloride.

An injectable dosage form of endo-N-(9-methyl-9-azabicyclo[3.3.1]non-3-yl)-1-methyl-1-indazole-3-carboxamide hydrochloride was first commercialized as a 1 mL single use vial containing an aqueous solution comprising 1.12 mg of granisetron hydrochloride equivalent to granisetron 1 mg. The recommended dosage for granisetron hydrochloride is 10 mcg/kg infused intravenously over 5 minutes, beginning within 30 minutes before initiation of chemotherapy.

The 1 mg/mL single dose vial has proved undesirable in a number of ways. The recommended dose is 10 mcg/kg of body weight. Thus, the 1 mL vial is not optimal for patients weighing greater than 100 kg, and a portion of a second vial will have to be utilized and the remaining medication discarded. Similarly, product wastage will occur when administering to lighter patients who do not require the full 1 mL dose. Numerous advantages are realized from a suitable multidose vial of endo-N-(9-methyl-9-azabicyclo[3.3.1]non-3-yl)-1-methyl-1H-indazole-3-carboxamide hydrochloride. The advantages of a multidose vial of endo-N-9-methyl-9-azabicyclo[3.3.1]non-3-yl)-1-methyl-1H-indazole-3-carboxamide hydrochloride include: making weight-based dosing more efficient thereby minimizing wasted product, conserving resources, containing costs, making better use of storage space and more cost-effective to produce and transport.

U.S. Pat. No. 6,294,548 discloses a multi-dose aqueous formulation of endo-N-(9-methyl-9-azabicyclo[3.3.1]non-3-yl)-1-methyl-1H-indazole-3-carboxamide hydrochloride and a host of possible preservatives, including meta-cresol, benzyl alcohol, methylparaben, propylparaben and a combination of methylparaben and propylparaben. According to the patent, the parabens are effective as preservatives, but unstable in autoclaving. Autoclaving is preferred by most regulatory agencies for ensuring sterility of pharmaceutical formulations.

It has now been found that certain combinations of preservatives and buffer systems yield formulations that are suitably stable during autoclaving. More particularly, it has been found that a pharmaceutical formulation comprising endo-N-(9-methyl-9-azabicyclo[3.3.1]non-3-yl)-1-methyl-1H-indazole-3-carboxamide hydrochloride, one or more preservatives selected from the group consisting of alkyl paraben and phenol, and a buffer selected from the group consisting of acetate and phosphate buffers can be autoclaved to yield a sterile multi-dose formulation.

DETAILED DESCRIPTION OF THE INVENTION

The parabens of the present invention are preferably $C_{1-4}$ alkyl parabens and salts thereof, which may be used alone or in combination with each other. Particularly preferred is methylparaben, in an amount of about 0.45 to 2.5 mg/mL and propylparaben, in an amount of about 0.05 to 0.45 mg/mL. The most preferred paraben preservative system is the combination of methylparaben and propylparaben, wherein the methylparaben is present in an amount of about 1.8 mg/mL and the propylparaben is present in an amount of about 0.2 mg/mL.

Where the preservative is phenol, it may be present in the formulation in an amount of 0.5 to 10 mg/mL, preferably about 5 mg/mL.

The buffer used in the pharmaceutical formulation of the present invention is an acetate or phosphate buffer. Preferred is an acetate buffer, which can be prepared from acetic acid and an acetate such as sodium, ammonium or potassium acetate. The amount of buffer employed in the formulation will be dictated by desired pH, with typical pHs ranging from 3.0 to 8.0, preferably 3.0 to 6.0.

The pharmaceutical formulation of the present invention can be sterilized by techniques known in the art, such as aseptic filtration (aseptic fill) or terminal heat sterilization (autoclaving). Terminal beat sterilization, such as by steam or cascading heated water, is, as previously noted, preferred to aseptic fill by most regulatory agencies. Sterilization can be measured by $F_o$, Sterilization Process Equivalent Time, which represents the equivalent number of minutes at 121.1° C. delivered to a container in a sterilization process. According to the present invention, sterilization is preferably carried out by autoclaving at a temperature from 115 to 125° C. for a period of 15 to 30 minutes, preferably at 121° C.±1° C. for a period of 19-24 minutes.

Buffer Selection Study

TABLE 1

Phosphate Buffer Formula

| Ingredient | Concentration (mg/mL) | Formulation Attribute |
|---|---|---|
| Granisetron HCl | 1.12 mg/mL* | Active agent |
| Sodium Chloride, USP | 9 | Tonicity agent |
| Sodium Phosphate Monobasic, Monohydrate, USP | 2.74 | Buffering agent |
| Sodium Phosphate Dibasic, Anhydrous, USP | 0.02 | Buffering agent |
| Purified Water, qs Ad | qs to 1 mL | Vehicle |

*equivalent to 1 mg of Granisetron base

TABLE 2

Acetate Buffer Formula

| Ingredient | Concentration (mg/mL) | Formulation Attribute |
|---|---|---|
| Granisetron HCl | 1.12 mg/mL* | Active agent |
| Sodium Chloride, USP | 9 | Tonicity agent |
| Glacial Acetic Acid, USP | 0.60 | Buffering agent |

TABLE 2-continued

Acetate Buffer Formula

| Ingredient | Concentration (mg/mL) | Formulation Attribute |
|---|---|---|
| Sodium Acetate, Anhydrous, USP | 0.82 | Buffering agent |
| Purified Water, qs Ad | qs to 1 mL | Vehicle |

*equivalent to 1 mg of Granisetron base

Procedure

In a suitable compounding vessel, add Purified Water equal to approximately 80% of batch size at room temperature. Then weigh and add Sodium Chloride, USP into the compounding vessel and mix until all is dissolved. Verify complete dissolution by visual inspection. Weigh and add the entire quantity of buffering agents as provided in Tables 1-2 for each formulation and mix until all is dissolved. Verify complete dissolution by visual inspection. Weigh and add the entire quantity of Granisetron HCl to the compounding vessel and mix until Granisetron HCl is dissolved. Measure pH. Qs the solution to final weight with purified water. Mix the bulk for not less than 5 minutes. Filter the solution through a sterilized 0.22 μm membrane filter. Fill the filtered solution into glass vials at 4 mL fill/vial and seal the vials with rubber stopper. Terminally sterilize the filled vials using a water cascade autoclave to a target $F_o$ of 30.

Results

The data reveals that all test results are satisfactory. A comparison of the assay and related compound results between the un-autoclaved and autoclaved samples from both the acetate and phosphate buffer formulae does not indicate any instability in either formulation.

Preservative Selection Study

TABLE 3

Parabens Formula

| Ingredient | Concentration (mg/mL) | Formulation Attribute |
|---|---|---|
| Granisetron HCl | 1.12 mg/mL* | Active agent |
| Sodium Chloride, USP | 9 | Tonicity agent |
| Glacial Acetic Acid, USP | 0.21 | Buffering agent |
| Sodium Acetate, Anhydrous, USP | 0.85 | Buffering agent |
| Methylparaben, NF | 1.8 | Preservative agent |
| Propylparaben, NF | 0.2 | Preservative agent |
| Purified Water, qs Ad | qs to 1 mL | Vehicle |

*equivalent to 1 mg of Granisetron base

TABLE 4

Phenol Formula

| Ingredient | Concentration (mg/mL) | Formulation Attribute |
|---|---|---|
| Granisetron HCl | 1.12 mg/mL* | Active |
| Sodium Chloride, USP | 9 | Tonicity Agent |
| Glacial Acetic Acid, USP | 0.52 | Buffering agent |
| Sodium Acetate, Anhydrous, USP | 0.82 | Buffering agent |
| Phenol, USP | 5.0 | Preservative agent |
| Purified Water, qs Ad | qs to 1 mL | Vehicle |

*equivalent to 1 mg of Granisetron base

Procedure

Compound a batch of Granisetron Hydrochloride Injection, 1.12 mg/mL, 4 mL fill/vial using the acetate buffer system. Add the selected preservative as listed above. Qs to final volume with purified water. Filter the solution using a 0.22 μm membrane filter. Fill the solution into glass vials and stopper using rubber stoppers (overlay vials containing phenol with nitrogen). Autoclave the filled vials at 121° C. to a $F_o$ of 15.

Results

The stability data reported below reveals that all test results are satisfactory. The stability evaluation is performed at accelerated stability conditions 40° C.±2° C./75%±5% RH for up to 3 months.

Granisetron assay data indicates no significant stability trends over a 3-month period at 40° C. No significant increase in degration products is observed. Methylparaben and propylparaben and phenol assays remain stable throughout the study. Antimicrobial preservative effectiveness testing is performed at the initial time point and all test results meet the USP <51> specification for an injectable product.

TABLE 5

Stability of Granisetron/Parabens Formulation

| Test | Unautoclaved | Autoclaved Initial | Autoclaved 40° C./75% RH 3 Months |
|---|---|---|---|
| Granisetron HCl | 99.6 | 100.4 | 101.3 |
| Degradation Product | Total: <0.05 | Total: 0.05 | Total = 0.05% |
| Methyl Paraben | 99.5 | 99.5 | 99.0 |
| Propyl parabens | 98.9 | 98.8 | 98.1 |

Formulation: Each mL contains Granisetron HCl 1.12 mg/mL, Sodium Chloride, USP 9 mg/mL, Glacial Acetic Acid, USP 0.52 mg/mL, Sodium Acetate Anhydrous, USP 0.82 mg/mL, Methylparaben, NF 1.8 mg/mL, Propylparaben, NF 0.2 mg/mL and Water for Injection qs to 1 mL.

TABLE 6

Stability of Granisetron/Phenol Formulation

| Test | Unautoclaved | Autoclaved Initial | Autoclaved 40° C./75% RH 3 Months |
|---|---|---|---|
| Granisetron HCl | 100.3 | 100.3 | 101.4 |
| Degradation Product | Total: <0.05 | Total: 0.05 | Total = 0.36% |
| Phenol | 99.3 | 100.5 | 102.4 |

Formulation: Each mL contains Granisetron HCl 1.12 mg/mL, Sodium Chloride, USP 9 mg/mL, Glacial Acetic Acid, USP 0.62 mg/mL, Sodium Acetate Anhydrous, USP 0.82 mg/mL, Phenol, USP 0.5 mg/mL and Water for injection qs to 1 mL

The invention claimed is:

1. A pharmaceutical formulation comprising endo-N-(9-methyl-9-azabicyclo[3.3.1]non-3-yl)-1-methyl-1H-indazole-3-carboxamide hydrochloride, a preservative of alkyl paraben, and an acetate buffer.

2. A formulation according to claim 1 wherein the preservative comprises one or more of a $C_{1-4}$ alkyl paraben and salts thereof.

3. A formulation according to claim 2 wherein the preservative comprises methylparaben and propylparaben.

4. A pharmaceutical formulation comprising endo-N-(9-methyl-9-azabicyclo[3.3.1]non-3-yl)-1-methyl-1H-indazole-3-carboxamide hydrochloride, a combination of methyl- and propylparaben as preservative, and an acetate buffer.

5. A pharmaceutical formulation comprising endo-N-(9-methyl-9-azabicyclo[3.3.1]non-3-yl)-1-methyl-1H-indazole-3-carboxamide hydrochloride, a preservative of phenol, and a buffer selected from the group consisting of acetate and phosphate buffers.

6. The formulation according to claim 5 wherein the formulation is a sterilized formulation.

* * * * *